(12) United States Patent
Christoffel et al.

(10) Patent No.: US 8,563,262 B2
(45) Date of Patent: Oct. 22, 2013

(54) PERMANENT INACTIVATION OF NUCLEASES

(75) Inventors: Gabriele Christoffel, Hilden (DE); Martin Schlumpberger, Hilden (DE); Heike Glowatz, Hilden (DE)

(73) Assignee: Qiagen GmbH, Hilden (DE)

( * ) Notice: Subject to any disclaimer, the term of this patent is extended or adjusted under 35 U.S.C. 154(b) by 351 days.

(21) Appl. No.: 12/680,515

(22) PCT Filed: Sep. 26, 2008

(86) PCT No.: PCT/EP2008/062977
§ 371 (c)(1), (2), (4) Date: Mar. 26, 2010

(87) PCT Pub. No.: WO2009/040431
PCT Pub. Date: Apr. 2, 2009

(65) Prior Publication Data
US 2010/0209993 A1    Aug. 19, 2010

(30) Foreign Application Priority Data

Sep. 27, 2007 (EP) .................................... 07019047

(51) Int. Cl.
*C12Q 1/44* (2006.01)
(52) U.S. Cl.
USPC .......................................................... 435/19

(58) Field of Classification Search
USPC ............................................................ 435/19
See application file for complete search history.

(56) References Cited

U.S. PATENT DOCUMENTS 6,281,349 B1    8/2001    Pulleyblank ................. 536/25.4

FOREIGN PATENT DOCUMENTS

EP          1 016 420 B1    7/2000
WO       WO 03/104251 A2   12/2003

OTHER PUBLICATIONS

Ahmad, Faizan et al., "The Denaturation of Ribonuclease A by Combinations of Urea and Salt Denaturants," *J. Mol. Biol.* 131(3):607-617, Jul. 5, 1979.
Chio, K.S. et al., "Inactivation of Ribonuclease and Other Enzymes by Peroxidizing Lipids and by Malonaldehyde," *Biochemistry* 8(7):2827-2832, Jul. 1969.
Scholtz, J. Martin et al., "Perchlorate-Induced Denaturation of Ribonuclease A: Investigation of Possible Folding Intermediates," *Biochemistry* 32(17):4604-4608, 1993.

*Primary Examiner* — Maryam Monshipouri
(74) *Attorney, Agent, or Firm* — Seed IP Law Group PLLC

(57) ABSTRACT

The present invention relates to the use of reagent for permanently inactivating nucleases wherein the reagent comprises an oxidizing agent, a protein denaturant and optionally a pH adjustor and to a method for permanently inactivating nucleases using said reagent.

21 Claims, 2 Drawing Sheets

Figure 1:
RNA positive control
Fig.1A
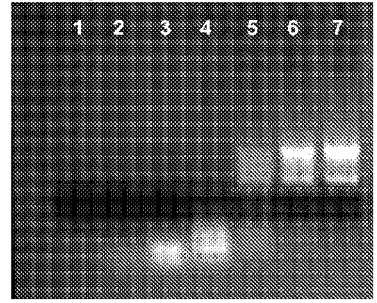
RNA negative control
Fig.1B
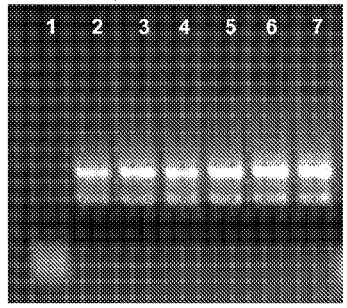
2%H2O2+0,5%SDS
Fig.1C
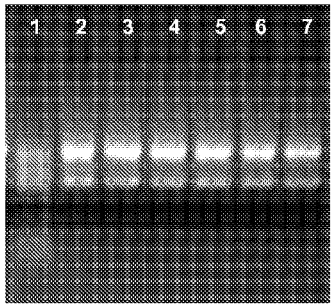
2%H2O2+1%SDS
Fig.1D
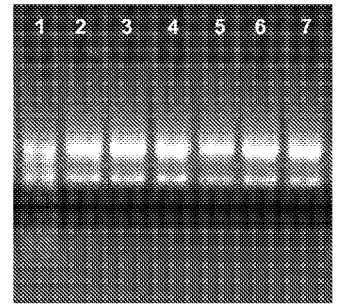
2%H2O2+2%SDS
Fig.1E
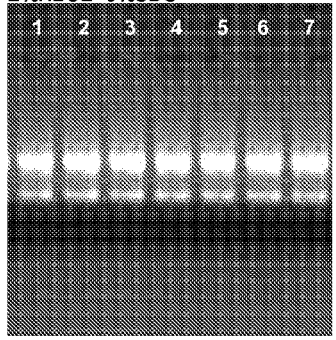
2%H2O2+5%SDS
Fig.1F
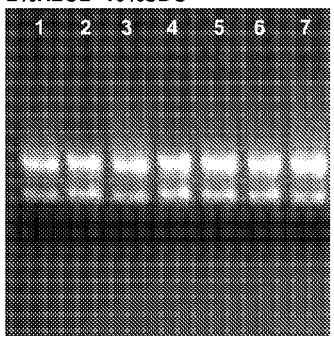
2%H2O2+10%SDS
Fig.1G
1 – RNA + 10 mg/ml RNase
2 – RNA + 1 mg/ml RNase
3 – RNA + 100 µg/ml RNase
4 – RNA + 10 µg/ml RNase
5 – RNA + 1 µg/ml RNase
6 – RNA + 100 ng/ml RNase
7 – RNA + 10 ng/ml RNase
8 – RNA

Figure 2:
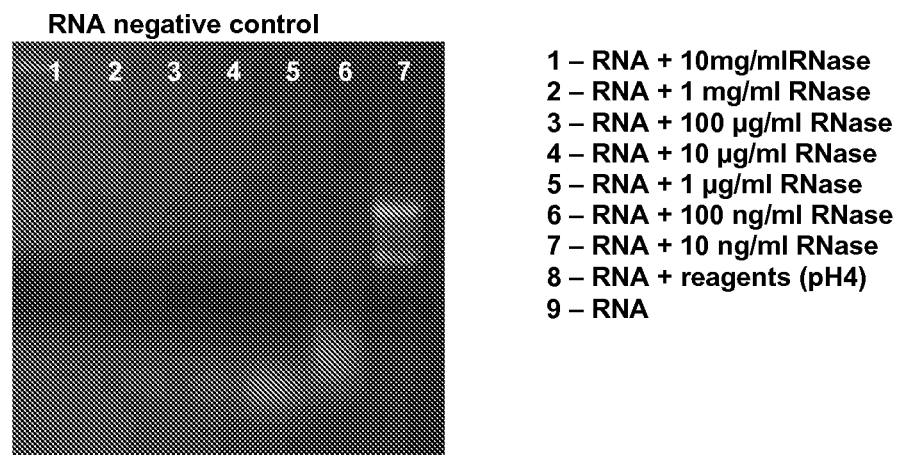
1 – RNA + 10mg/ml RNase
2 – RNA + 1 mg/ml RNase
3 – RNA + 100 µg/ml RNase
4 – RNA + 10 µg/ml RNase
5 – RNA + 1 µg/ml RNase
6 – RNA + 100 ng/ml RNase
7 – RNA + 10 ng/ml RNase
8 – RNA + reagents (pH4)
9 – RNA
Fig.2A
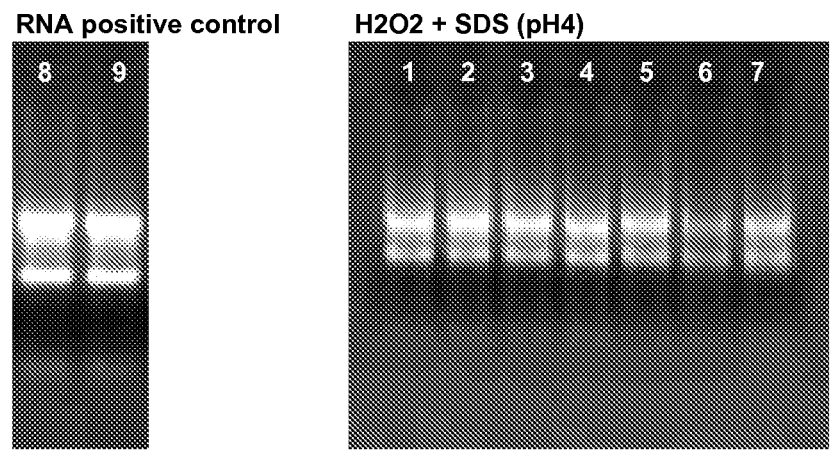
Fig.2B   Fig.2C

PERMANENT INACTIVATION OF NUCLEASES

This application is a 371 of PCT/EP08/62977, filed 9/26/2008, which claims foreign priority to European Patent Application (EPO) 07019047.5, filed 9/27/2007.

TECHNICAL FIELD

The present invention generally relates to the field of molecular biology. More particularly, it concerns the permanent inactivation of nucleases, comprising ribonucleases (RNases) which can degrade RNA and deoxyribonucleases (DNases), which can degrade DNA.

The quality of an RNA or DNA preparation greatly affects the results obtained when analyzing RNA or DNA by a number of different molecular biology techniques such as northern- or southern-blotting, ribonuclease protection assays, PCR and RT-PCR (Reverse Transcription-Polymerase Chain Reaction). Degraded RNA or DNA leads to lower signals compared to equivalent intact RNA or DNA samples. Compared to DNA, RNA is much more susceptible to degradation (Sambrock 1989). It is readily decomposed when exposed to conditions of extreme pH or in the presence of metal ions and high temperatures. The principal reason for nucleic acid degradation, however, is given by the impact of nucleases. Therefore an adequate guard against nucleases during handling of RNA or DNA is of great importance. Nuclease contamination can derive from cell and tissue samples, skin secretions or microorganisms transmitted by airborne dust particles. Reasonable precautions must be followed to obtain a nuclease-free environment during working with RNA and DNA (Blumberg (1987), Methods Enzymol., 152:20-24). Nucleases not only contaminate the manual working space but are also a common contamination in molecular biology instruments like the biorobot systems, especially in systems used infrequently. The appearance of nucleases in automated systems may be ascribed to the development of biofilms inside the tubing and gaskets of the systems. Microorganisms contained in these biofilm formations may produce nucleases next to other bio-molecules.

RELEVANT PRIOR ART

Several, mostly inefficient approaches to inactivate nucleases exist. Since some nucleases show low activity at high temperature, heating is used as an approach to inactivate nucleases. However, subsequent reduction of the temperature typically leads to a fully restored nuclease activity. For cleaning of glassware, baking at 180° C. for 8 hours or more or for plastic ware rinsing with chloroform is recommended.

Another approach is to incubate glass- or plastic ware for 2 hours at 37° C. in a 0.1% solution of diethyl pyrocarbonate (DEPC), rinse afterwards several times with DEPC treated water and autoclave for 15 min (Blumberg (1987), Methods Enzymol., 152:20-24 Working with DEPC, however, is not recommendable since it is expensive and probably carcinogenic. Furthermore baking of instruments and/or treatment with DEPC is time consuming and not always possible.

Some prior art uses ribonuclease inhibitors during RNA handling (WO-A-01/21830, US-A-2005/0214839, WO-A-2005/083081) but none of these describes a complete and permanent, irreversible, destruction of ribonucleases, which would be more convenient than just an inhibitory effect. In addition to the fact that pure ribonuclease inhibitor solutions will not permanently remove ribonucleases from a system, they will not have any effect on ribonucleases, once the inhibitor solution was removed from the system. Proteinaceous nuclease inhibitors are also prohibitively expensive to be widely used for workplace decontamination.

Some prior art uses the denaturing effects of extreme pH to permanently inactivate and destroy ribonucleases (e.g. LTK-008™ from Biodelta, pH≈11; Exitusplus™ from AppliChem, pH≈2). On the other hand, such treatments necessarily lead to the destruction of ribonucleic acids and deoxyribonucleic acids as well. Some nucleases even withstand autoclaving, extreme pH values or the protein denaturant urea (Spackman 1960). A combination of NaOH and ethylenediamine tetra-acetic acid (EDTA) or sodium dodecyl sulphate (SDS) is commonly used for cleaning, e.g. of biorobot systems. SDS denatures proteins at room temperature, allowing a shorter incubation time. NaOH in combination with SDS is also used to denature chromosomes, plasmid DNA and proteins, and to lyse micororganisms. Since EDTA is a chelating agent, it can on one hand be used to inhibit enzymes which are depended on divalent ions for their activity and on the other hand help to destroy the cell membrane. SDS and EDTA, however, only lead to an inhibitory effect but not to an irreversible destruction of the ribonucleases since denaturation by SDS is reversible (Weber, K. & Kuter, D. J. (1971). J. Biol. Chem. 248 (14): 4504-4509). Furthermore, EDTA is not always helpful for inactivation, since not all nucleases (especially ribonucleases) need divalent ions for their activity.

In case of an intense nuclease contamination, e.g. due to the development of a biofilm, consisting of an extra cellular polymer substance which, in combination with water, builds a mucous matrix, cleaning with an NaOH/EDTA solution is insufficient in most cases. Bacteria or other organisms (e.g. algae), existing in these biofilms, are able to produce nucleases and release them into the system, leading to degraded nucleic acids. This source of nuclease contamination is not easy to remove since the extra cellular polymer substance of the biofilm consists of polysaccharides, proteins, lipids and nucleic acids, which protect the microorganisms accommodated inside from chemicals 10 to 10000 times more compared to planktonic microorganisms (Gilbert, P., Das, J. R., Jones, M V., & Allison, D. G. (2001). J. Appl. Microbiol., 91: 248-254.). Accordingly, to clear all nuclease contamination from the systems, a complete removal of possible biofilms is necessary.

SDS can dissolve the cell membrane of microorganisms, making destruction of nuclease-releasing organisms possible. The same is true for $H_2O_2$ since it attacks the unsaturated fatty acids embedded in the membrane structure. $H_2O_2$ is a common biocide contained in several commercially available disinfectant products, e.g. Proxitane® (Solvay PAA, Cheshire, UK) or Accepta 8101 (Accepta™, Manchester, UK). Nevertheless $H_2O_2$ is sensible to catalyse activity, which is very high in gram negative bacteria. Several publications indicate that catalase activity complicates the destruction of a biofilm because of its ability to decompose $H_2O_2$.

OBJECT OF THE PRESENT INVENTION

The technical problem underlying the present invention is to provide a method for permanent inactivation of nucleases, suitable for the entire working environment including the manual working space as well as molecular biology instruments or systems like biorobots. It is a further objective of the present invention to be able to kill microorganisms, which are a source of nuclease production, no matter if they appear individually or are organised in a biofilm. It is a further aim underlying the present invention that ribonucleic acids or deoxyribonucleic acids are not degraded or destroyed and that the reagent is not hazardous for the exposed user.

BRIEF DESCRIPTION OF THE DRAWINGS

FIG. 1A shows a control gel wherein step a) of Example 1 was left out so that no ribonuclease solution was added (positive control).

FIG. 1B shows a negative control gel wherein step c) of Example 1 was left out so that no reagent according to the invention was applied (negative control).

FIG. 1C shows a gel wherein all protocol steps a) to f) of Example 1 were performed.

FIGS. 1D-1G show gels demonstrating the effects of concentrations of SDS other than the concentration shown in FIG. 1C.

FIG. 2A shows a control gel wherein step b) of Example 2 was left out so that no reagent according to the invention was applied (negative control).

FIG. 2B shows a control gel wherein step c) of Example 2 was left out so that no ribonuclease solution was added (positive control).

FIG. 2C shows a gel wherein all steps a) to d) of Example 2 were performed.

DETAILED DESCRIPTION OF THE PRESENT INVENTION

The above mentioned problems are solved by using a preferably aqueous reagent (composition) according to the invention which comprises an oxidizing agent and a protein denaturant for permanently inactivating nucleases.

In a preferred embodiment the oxidizing agent is selected from peroxides, preferably from a group consisting of $H_2O_2$, alkaliperoxides, peroxosulfates, peroxophosphates, peracids, preferably peracetic acid or ozone, oxoanions like permanganate or dichlorate, hypochloride (hypochlorite), chlorate and corresponding compounds of other halogens, perchlorate and mixtures thereof, and the protein denaturant is selected from surfactants. The surfactants should exhibit protein denaturing properties and can be exemplified by detergents, in particular anionic, cationic, amphoteric or nonionic detergents.

In a preferred embodiment, said oxidizing agent is $H_2O_2$. This compound has the additional advantage that it does not leave any residues after reaction, except water. In a further preferred embodiment the protein denaturating agent is represented by SDS.

Particularly, the reagent/composition of the present invention comprises a combination of $H_2O_2$ and SDS.

According to a more preferred embodiment of the present invention the concentration of the oxidizing agent—for example $H_2O_2$—is in the range of 1% to 40% by volume. In an even more preferred embodiment concentration of $H_2O_2$ is in the range of 1.5 to 16% by volume. In the most preferred embodiment $H_2O_2$ is present in the reagent in a concentration of 2% by volume.

In another embodiment said protein denaturant—for example SDS—is present in the reagent with a concentration in the range of 0.5% to 15% by volume. In a more preferred embodiment SDS is present in a concentration in the range of 1% to 6% by volume. In an even more preferred embodiment SDS is present with a concentration of 5% by volume.

In an utmost preferred embodiment the reagent comprises a mixture of $H_2O_2$ with a concentration of 2% by volume and SDS with a concentration of 5% by volume.

In order to ensure a high oxidation potential of the oxidizing agent it is recommended to adapt the pH of the mixture accordingly. For example, a low pH value is recommended if $H_2O_2$ is supposed to function as the oxidizing agent, i.e. the pH is adjusted to ≤11. In a more preferred embodiment, the pH is adjusted to ≤7 and in an even more preferred embodiment the pH is adjusted to ≤5. Moreover, it might have advantages to adjust the pH value such that it is not too low. In particular the less acidic the mixture is the less hazardous and corrosive it is supposed to be. Therefore, in a preferred embodiment the pH value is ≥2, more preferred ≥3 and most preferred ≥4. The pH of the reagent can be adjusted with any chemical compound—pH-adjustor—which is capable for changing the pH value of aqueous solutions and which does not negatively influence the activity of the oxidizing agent and the protein denaturant. Examples are well known in the art and encompass inorganic (mineral acids) or organic acids, inorganic or organic bases, salts of the above mentioned acids and bases as well as mixtures of these in buffer systems. It is particularly advantageous to select compounds which may function as buffering agents as well as chelating agents. Examples for suitable pH adjusters are citric acid, tartaric acid, acetic acid, phthalic acid, phosphoric acid, succinic acid, hydroxysuccinic acid, oxalic acid and mixtures thereof.

It is preferred that the reagent comprises water. However, it is also possible that it comprises in addition to or instead of water one or more organic solvents which also are suitable for the intended purpose.

The composition may additionally contain other ingredients like colorants, stabilizing agents, scents and other components which might provide properties desired for treating, cleaning and/or decontaminating surfaces or compositions or mixtures of any of those compounds. It is particularly preferred to add stabilizing agents which prevent the decomposition of the oxidizing agent. When the oxidizing agent is realized by $H_2O_2$ a suitable stabilizing agent might be able to complex ions supporting the catalytic decomposition of $H_2O_2$. Examples for such stabilizing agents are chelating agents like ethylenediamine (en), diethylenetriamine (dien), iminodiacetate (ida), diethylenetetraamine, triaminotriethylamine, ethylenediaminotriacetate, ethylenediaminetetraacetate EDTA), [ethylenebis(oxyethylenenitrilo)]tetraacetic acid (EGTA), dimethylglyooxime (dmg), 8-hydroxyquinoline, 2,2'-bipyridine (bpy), 1,20-phenanthroline (phen), dimercaptosuccinic acid and mixtures thereof. Preferably the stabilizing agents are contained in the composition in a total amount of from 0.5 to 100 mmol/l, more preferred from 1 to 50 mmol/l, further preferred from 2 to 10 mmol/l and most preferred from 4 to 6 mmol/l based on the complete composition.

The method according to the invention is carried out at room temperature (RT), which covers a temperature range of about 15° C. to about 30° C.

The method according to the invention is carried out with an incubation time of the reaction mixture in a range of about 1 to about 20 min.

While being efficient in permanently inactivating nucleases and microorganisms, the reagent in a preferred embodiment, comprising 5% by volume SDS and 2% by volume $H_2O_2$ with pH ≥4, is at the same time safe enough for handling and does not pose a threat to the exposed user.

EXAMPLE 1

The following example is adequate for testing the efficiency of the disclosed method. Briefly, after contamination with ribonucleases the reagent according to the invention is applied to the contaminated equipment. RNA probes contacted thereafter with the cleaned equipment are no more decomposed.

Detailed Protocol:
a) At first, a ribonuclease contamination is intentionally effected by adding 20 µl of differently concentrated ribonuclease solutions [10 mg/ml, 1 mg/ml, 100 µg/ml, 10 µg/ml, 1 µg/ml, 100 ng/ml, 10 ng/ml] to different reaction tubes and incubating the tubes for 15 min at RT.
b) Subsequently, the ribonuclease solutions are removed and the reaction tubes—are air-dried.
c) 30 µl of the reagent according to the invention, comprising 2% $H_2O_2$ and different amounts of SDS (0.5-10%) pH 4, are added to each reaction tube and incubated for 5 min at RT.
d) Subsequently, the reagent is removed and the reaction tubes are air-dried.
e) 10 µl of a 0.3 µg/µl RNA solution (prepared in ribonuclease-free water) are added to each reaction tube and incubated for 15 min at RT.
f) After adding 3 µl of a blue RNA marker to each reaction tube, the solutions are tested on a 1.2% formaldehyde gel.

In FIG. 1A, a control gel is displayed, wherein step a) was left out so that no ribonuclease solution was added (positive control).

In FIG. 1B, a control gel is displayed, wherein step c) was left out so that no reagent according to the invention was applied (negative control).

In FIG. 1C, the bands resulting after applying all protocol steps a) to f) are displayed. This result demonstrates the efficiency of the disclosed method, since the quality of all bands in every lane is comparable to the quality of the bands of the positive control displayed in FIG. 1A. FIGS. 1D-1G show the effects of other concentrations of SDS.

EXAMPLE 2

The following example provides another way for testing the efficiency of the disclosed method. Briefly, RNA and the reagent according to the invention are added to reaction tubes. Subsequent RNase contamination of the RNA and reagent does not lead to the decomposition of the RNA.

Detailed Protocol:
a) 4 µl of a 4 µg/µl RNA solution (prepared in ribonuclease-free water) are added to different reaction tubes
b) 4 µl of a reagent according to the invention, comprising 10% SDS and 30% $H_2O_2$, pH=4, is added to the reaction tubes and incubated for 5 min at RT.
c) Subsequently, 1 µl of differently concentrated ribonuclease solutions [10 mg/ml, 1 mg/ml, 100 µg/ml, 10 µg/ml, 1 µg/ml, 100 ng/ml, 10 ng/ml] are added and incubated for 15 min at RT.
d) After adding 3 µl of a blue RNA marker, the solutions are tested on a 1.2% formaldehyde gel.

In FIG. 2A, a control gel is displayed, wherein step b) was left out so that no reagent according to the invention was applied (negative control).

In FIG. 2B, a control gel is displayed, wherein step c) was left out so that no ribonuclease solution was added (positive control).

In FIG. 2C, the resulting bands after applying all steps a) to d) are displayed. Since the quality of all bands in every lane is comparable to the quality of the bands of the positive control displayed in FIG. 2A, the efficiency of the disclosed reagent for the indicated use is confirmed.

The invention claimed is:

1. A method for permanently inactivating nucleases, comprising:
   a) providing a reagent comprising an oxidizing agent, a protein denaturant, and optionally a pH adjustor,
   b) bringing the nucleases into contact with said reagent, and
   c) contacting said nucleases and said reagent for a time and at a temperature sufficient to permanently inactivate the nucleases.

2. The method according to claim 1, wherein said oxidizing agent is selected from the group consisting of peroxides, alkaliperoxides, peroxosulfates, peroxophosphates, peracids, ozone, oxoanions, and combinations thereof.

3. The method according to claim 1, wherein said peroxide is hydrogen peroxide ($H_2O_2$).

4. The method according to claim 3, wherein said $H_2O_2$ is present in a concentration in the range of 1 to 40% by volume.

5. The method according to claim 1, wherein said protein denaturant is one or more surfactants.

6. The method according to claim 5, wherein said surfactant is sodium-dodecyl-sulphate (SDS).

7. The method according to claim 6, wherein said SDS is present in a concentration in the range of 0.5 to 15% by volume.

8. The method according to claim 1, wherein said reagent comprises $H_2O_2$ and SDS at concentrations of 2% and 5% by volume, respectively.

9. The method according to claim 1, wherein the pH of said reagent is adjusted to ≤11.

10. The method according to claim 1, wherein said reagent is applied for a time in a range of about 1 to about 20 minutes.

11. The method according to claim 1, wherein the method is performed at a temperature in a range of 15° C. to 30° C.

12. The method of claim 2, wherein the peracid is peracetic acid.

13. The method of claim 2, wherein the oxoanion is selected from permanganate; dichlorate, hypochloride, chlorate, perchlorate, and corresponding compounds of other halogens; and combinations thereof.

14. The method of claim 3, wherein said $H_2O_2$ is present at a concentration in the range of 1.5 to 16% by volume.

15. The method of claim 3, wherein said $H_2O_2$ is present at a concentration of 2% by volume.

16. The method of claim 5, wherein said protein denaturant is a denaturing detergent.

17. The method of claim 16, wherein said denaturing detergent is selected from anionic detergents, cationic detergents, amphoteric detergent, non-ionic detergents, and combinations thereof.

18. The method of claim 7, wherein said SDS is present in a concentration in the range of 1 to 10% by volume.

19. The method of claim 7, wherein said SDS is present in a concentration of 5% by volume.

20. The method of claim 9, wherein the pH of said reagent is adjusted to ≤7.

21. The method of claim 9, wherein the pH of said reagent is adjusted to ≤5.

* * * * *